(12) United States Patent
Mayer et al.

(10) Patent No.: US 12,171,478 B2
(45) Date of Patent: Dec. 24, 2024

(54) APPARATUS AND METHOD FOR SUPPLYING COOLANT TO A MEDICAL INSTRUMENT

(71) Applicant: Erbe Elektromedizin GmbH, Tuebingen (DE)

(72) Inventors: Volker Mayer, Tuebingen (DE); Frank Straub, Tuebingen (DE); Martin Georg Fritz, Tuebingen (DE); Waldemar Wandel, Kusterdingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 402 days.

(21) Appl. No.: 17/149,284

(22) Filed: Jan. 14, 2021

(65) Prior Publication Data

US 2021/0228254 A1 Jul. 29, 2021

(30) Foreign Application Priority Data

Jan. 23, 2020 (EP) .................................... 20153421

(51) Int. Cl.
*A61B 18/02* (2006.01)
*A61B 18/00* (2006.01)

(52) U.S. Cl.
CPC .... *A61B 18/02* (2013.01); *A61B 2018/00172* (2013.01); *A61B 2018/00714* (2013.01); *A61B 2018/00773* (2013.01); *A61B 2018/025* (2013.01); *A61B 2018/0256* (2013.01); *A61B 2018/0262* (2013.01)

(58) Field of Classification Search
CPC ............ A61B 18/02; A61B 2018/0262; A61B 2018/0256; A61B 2018/025; A61B 2018/0237; A61B 2018/00863
See application file for complete search history.

(56) References Cited

U.S. PATENT DOCUMENTS

| | | | |
|---|---|---|---|
| 4,275,734 A | 6/1981 | Mitchiner | |
| 6,635,053 B1 * | 10/2003 | Lalonde | A61B 18/02 606/22 |
| 2002/0007180 A1 * | 1/2002 | Wittenberger | A61B 18/02 607/113 |
| 2002/0068929 A1 | 6/2002 | Zvuloni | |
| 2009/0171333 A1 | 7/2009 | Hon | |

(Continued)

FOREIGN PATENT DOCUMENTS

| | | |
|---|---|---|
| CN | 105972853 A | 9/2016 |
| CN | 109431594 A | 3/2019 |

(Continued)

*Primary Examiner* — Daniel W Fowler
(74) *Attorney, Agent, or Firm* — Blank Rome LLP (57) ABSTRACT

An apparatus for supply of coolant, particularly $CO_2$ that is preferably provided in bottles, to cryosurgical instruments. The device may be a mechanical or thermal compression device. A pump may supply the $CO_2$ taken from the bottle in a buffer container with a desired operation pressure. The pressure in the gas bottle can be less than the desired operation pressure. The apparatus includes a tempering device that is configured to bring the coolant to a desired temperature, particularly a temperature that is higher than the temperature in the gas bottle or in another storage container.

14 Claims, 6 Drawing Sheets

(56) References Cited

U.S. PATENT DOCUMENTS

| | | | |
|---|---|---|---|
| 2009/0299356 A1* | 12/2009 | Watson | A61M 25/1006 |
| | | | 606/21 |
| 2014/0066913 A1* | 3/2014 | Sherman | A61B 18/1492 |
| | | | 606/41 |
| 2014/0163538 A1* | 6/2014 | Ryba | A61F 7/0085 |
| | | | 606/21 |
| 2014/0276698 A1* | 9/2014 | Wittenberger | A61B 18/02 |
| | | | 606/21 |
| 2014/0276706 A1* | 9/2014 | Duong | A61B 18/02 |
| | | | 606/21 |
| 2015/0342660 A1* | 12/2015 | Nash | A61B 18/02 |
| | | | 606/21 |
| 2018/0199979 A1 | 7/2018 | Mahrouche et al. | |
| 2018/0303535 A1* | 10/2018 | Yu | A61B 18/02 |
| 2019/0000524 A1* | 1/2019 | Rosen | A61F 7/0085 |
| 2019/0328437 A1* | 10/2019 | Perron | A61B 18/02 |
| 2020/0003364 A1* | 1/2020 | Harmouche | F17C 6/00 |

FOREIGN PATENT DOCUMENTS

| | | | |
|---|---|---|---|
| CN | 110215274 A | 9/2019 | |
| CN | 110215275 A | 9/2019 | |
| DE | 10 2016 006 132 A1 | 11/2017 | |
| FR | 2 981 268 A1 | 4/2013 | |
| JP | S5540336 A | 3/1980 | |
| JP | 2011508629 A | 3/2011 | |
| JP | 201334798 A | 2/2013 | |
| RU | 2 609 056 C1 | 1/2017 | |

\* cited by examiner

APPARATUS AND METHOD FOR SUPPLYING COOLANT TO A MEDICAL INSTRUMENT

CROSS REFERENCE TO RELATED APPLICATION

This application claims priority to European Application No. 20153421.1, filed Jan. 23, 2020, the entirety of which is incorporated by reference herein.

TECHNICAL FIELD

Embodiments described herein include an apparatus and a method for supplying coolant to a medical instrument.

BACKGROUND

For supply of coolant to medical instruments, US 2002/0068929 A1 proposes to compress gas taken from a pressure bottle by means of a piston pump. This compression makes particularly sense, if the gas pressure in the storage bottle reduces gradually, such that it is insufficient for the operation of a cryoinstrument or another consumer. Therefore, the gas content of the bottle is only used incompletely. By means of the piston pump, however, gas can be provided with the desired pressure, also if the pressure in the storage bottle has decreased below the desired pressure.

However, with gases that are provided as saturated vapor, the pressure increase can result in failures in the instrument or also in other aggregates, as for example pressure controllers, valves or the like.

SUMMARY

It is the object of embodiments of the invention to provide an apparatus and a method for supply of coolant to a medical instrument with which the appropriate operation of the instrument is also guaranteed, if the pressure of a coolant contained in a storage container is less than required for the operation of the instrument.

This object is solved by an apparatus according to claim 1 and a method according to claim 14:

The apparatus according to embodiments of the invention comprises a storage container for a coolant supply or a connection for such a storage container in which the coolant is provided in compressed condition. In addition, embodiments of the inventive apparatus comprises a buffer container in which additional coolant supply can be provided. The coolant is also under pressure in the buffer container, wherein this pressure is higher or can be higher than the pressure in the storage container.

Also a tempering device is provided that is at least connected with the buffer container in order to influence its temperature. In this manner it can be ensured that the coolant supplied to the instrument is provided in the desired gaseous, liquid or superfluid phase and is under the necessary pressure. If the instrument is configured for operation with gaseous compressed coolant, due to the tempering of the coolant, e.g. due to specific heating thereof, it is avoided that droplets condense from the coolant that could impede the function in pipes, valves or in the instrument. For this the tempering device can be configured as heating device. In addition, the tempering device can be provided to build up the desired pressure in the buffer container that can be higher than the pressure in the storage container.

Inversely, because of tempering of the coolant, it is also possible to control the temperature of the coolant for instruments that have to be operated with liquid coolant, such that the liquid coolant does not form vapor bubbles at undesired locations in the pipes, valves or in the instrument that could affect the function. For this the tempering device can be configured as cooling device, for example.

The coolant can be subject to a thermal compression in that it is heated by means of the tempering device in the buffer container under volume containment. In addition or as an alternative, it can be subject to a mechanical compression in that it is compressed by means of a mechanical pump.

For providing the coolant in a buffer container with the desired pressure, i.e. for mechanical compression, a pump can be provided in addition to the tempering device that is connected with the storage container on its suction side and with the buffer container on its pressure side. Then the pump compresses coolant taken from the storage container and supplies it to the buffer container with increased pressure.

In the storage container the coolant, e.g. $CO_2$ or another gas that can be simply liquefied, can be provided at least in one part in liquid phase and in another part in gaseous phase. It can be taken from the storage container in liquid or—as it is mostly preferred—in gaseous phase. If it is provided in the storage container in liquid as well as in gaseous phase, the gaseous phase forms saturated vapor from which coolant droplets can condense in case of pressure increase or cooling.

Also in the buffer container the coolant can be provided partly in liquid and partly in gaseous phase or alternatively exclusively in gaseous phase or exclusively in liquid phase. The buffer container serves predominantly for intermediate storage of coolant for tempering thereof as well as for pressure compensation in order to avoid pressure oscillations resulting from the pump and in order to provide coolant for further use in the context of which it is supplied via a pressure control valve first, for example.

Due to tempering at least the buffer container, but preferably also the pressure control valve (if present), the pump and potential pipes connecting these elements, it is achieved that the coolant is distanced from the liquid gaseous phase boundary. If the coolant is, for example, $CO_2$ and if an operation pressure of, e.g. 55 bar is required, the coolant cannot be safely taken from a gas bottle serving as storage container in each case under the desired pressure. For example, a gas bottle supplies $CO_2$ at 15° C. only with a pressure of 51 bar. In the apparatus according to embodiments of the invention, the coolant ($CO_2$) is however reliably provided under such conditions with the necessary pressure, namely by pressure increase by means of the pump and tempering of the coolant compressed to a higher pressure.

For example, the apparatus can comprise a vapor saturation sensor in a pipe leading to the supply connection that is connected with the control device of the apparatus. The vapor saturation sensor detects the condition of the coolant and creates a respective signal. The control device can be configured to control the tempering device or potential pumps and valves, such that the desired vapor saturation is achieved. The vapor saturation sensor can be arranged before or after a potential pressure valve.

The tempering of the coolant in the pump, the buffer container and/or the pressure controller can comprise a heating and/or also cooling of the coolant, particularly if the coolant has to be provided in liquid condition to the instrument. In this case the coolant is distanced from the liquid gaseous phase boundary by cooling or—if the distance to the phase boundary gets too high, due to the pressure increase—it is approached to the phase boundary by heating.

The tempering device can be a heating device or a cooling device or a combined heating and cooling device depending on the application. The heating and cooling device can be formed by one or more Peltier-elements that are thermally coupled with the at least one buffer container. If it is operated for cooling, it effectuates the flow of coolant in the buffer container. The coolant increases its density due to cooling and can condense, if it is cooled sufficiently. If the Peltier-element is subsequently operated for heating and if the buffer container is thus far closed such that no coolant can flow back to the storage container, the pressure of the coolant increases.

All in all, embodiments of the invention provides an apparatus and a method with which the pressure of the coolant can be brought to a desired value independent from the pressure in a storage container, wherein a desired distance to the liquid gaseous phase boundary can be adjusted by means of tempering of the coolant or this distance can be kept in a desired range. This applies for liquid as well as gaseous coolants, wherein the operation safety of cryosurgical instruments can be remarkably increased also under adverse conditions, e.g. at particularly low or also high environment temperatures. Particularly the operation safety of the instrument is facilitated independent from the temperature of a coolant storage container, e.g. a gas bottle.

BRIEF DESCRIPTION OF THE DRAWINGS

Details of embodiments of the invention are apparent from the following description and the assigned figures, as well as dependent claims. The drawings show:

DETAILED DESCRIPTION

Figure 1:
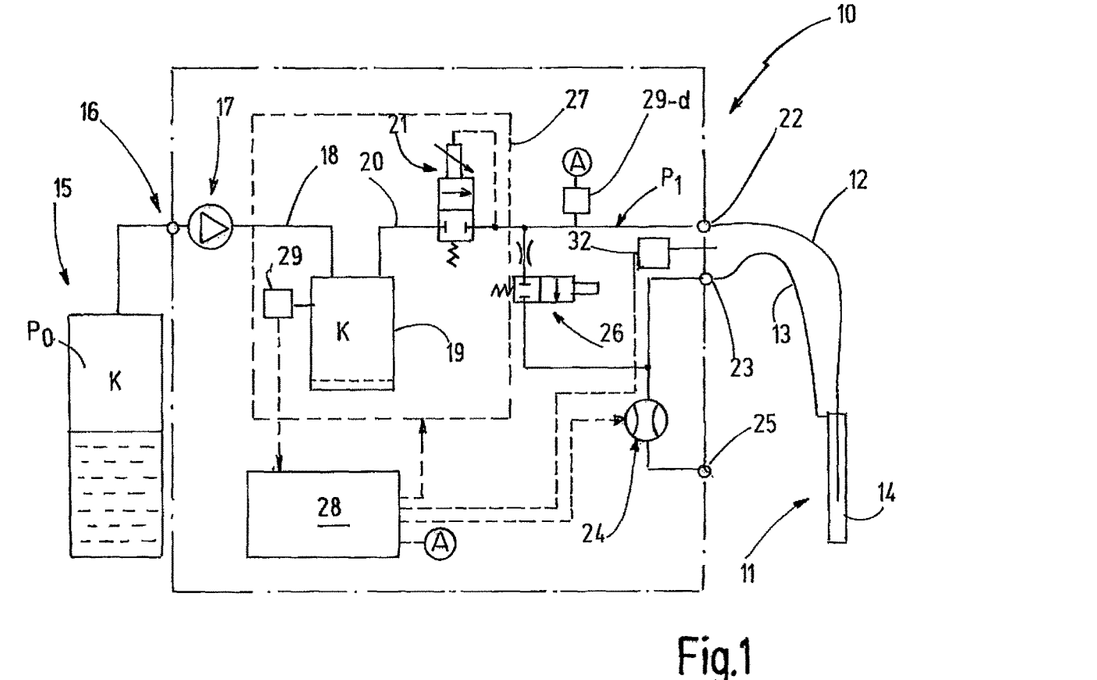
FIG. 1 shows an embodiment of an inventive apparatus for supply of coolant to a medical instrument in a schematic and simplified illustration.

FIG. 1 exemplarily illustrates an apparatus 10 for supply of a cryosurgical instrument 11 to which a coolant K is supplied via a pipe 12 and returned via a pipe 13. Thereby the coolant K is supplied to the instrument 11 under pressure, wherein it expands in an expansion chamber 14 of the instrument 11 in order to create cold. The creation of cold can be particularly based on the Joule-Thomson-effect in which the expansion of a gaseous coolant K at a restrictor results in cooling.

Figure 6:
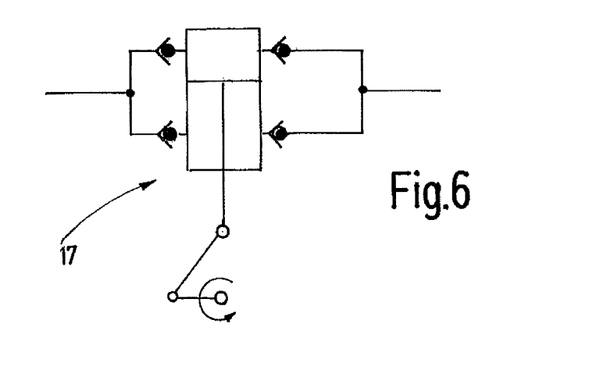
FIG. 6 shows an embodiment of a pump of the inventive apparatus.

A storage container 15, for example a gas bottle, serves for providing coolant K and is connected with the apparatus 10 via a connection 16 in order to supply gaseous coolant K thereto. Thereby the gas bottle is subject under a temperature-dependent pressure that can have an amount of, for example, 51 bar at 15° C. and about 64 bar at 25° C. The pressure $P_1$ of the coolant K that has to be supplied to the instrument 11 shall have an amount of 55 bar, for example. In order to ensure this independent from the pressure $P_0$ in the storage container 15, the apparatus 10 uses mechanical compression and for this comprises, for example, a pump 17 (pressure increase pump) that is connected via the connection 16 with the storage container 15 on the suction side and via a pipe 18 with a buffer container 19 on the pressure side. The pump 17 is exemplarily illustrated in FIG. 6. It is configured as double-acting piston pump, the piston of which has to provide only a pressure difference between the storage container 15 and the buffer container 19. However, also other pumps are suitable, particularly displacement pumps, e.g. piston compressor, double piston compressor, screw compressor, diaphragm pump or also a turbo-compressor.

A pipe 20 leads from the buffer container 19, preferably via a pressure control valve 21 to a supply connection 22, connected with the pipe 12. The pipe 13 forming the return is, however, coupled with a return connection 23 that leads to an outlet 25 via a flow controller (mass flow controller) 24. An activation valve 26 serves for activation or deactivation of the instrument 11, for example the activation valve 26 opens or closes a bypass between the supply and the return.

In addition the apparatus 10 comprises a tempering device 27 that is assigned at least to the buffer container 19, but preferably also to the pipes 18, 20 and the pressure control valve 21 that is thermally coupled therewith. The tempering device 27 is thermally coupled with the buffer container 19, the pipes 18, 20 and the pressure control valve 21 in order to influence their temperature. As an option, the tempering device 27 can also be in thermal contact with the pump 17 and if necessary, also with a pipe connecting the pressure control valve 21 with the supply connection 22. In the simplest case the tempering device 27 is a heating device that serves to bring the elements that are in thermal contact therewith to a desired temperature and to maintain it. However, it can also be configured as cooling device or as combined heating and cooling device.

A control device 28 is provided for control of the apparatus 10 and particularly the tempering device 27 being connected to the control device 28. The tempering device 27 consists, for example, of one or more heating elements that are attached to the components and units to be heated, for example the pump 17 and/or the pipe 18 and/or the buffer container 19 and/or the pipe 20 and/or the pressure control valve 21. The control device 28 can be additionally connected with a sensor 29 for determination of the pressure and/or the temperature of the coolant K in the buffer container 19. Similarly the control device 28 can be connected with the activation valve 26 of the pump 17 and/or the flow controller (mass flow controller) 24.

For explanation of the operation of the apparatus 10 and the instrument 11 connected thereto, it is assumed that the instrument 11 has to be supplied with $CO_2$ as coolant K under a pressure of, for example, 55 bar, wherein the coolant has to be provided in gaseous condition. It is further assumed that the gas bottle forming the storage container 15 comprises a temperature of only 15° C. and the coolant K is thus provided under a pressure of only 51 bar.

Figure 5:
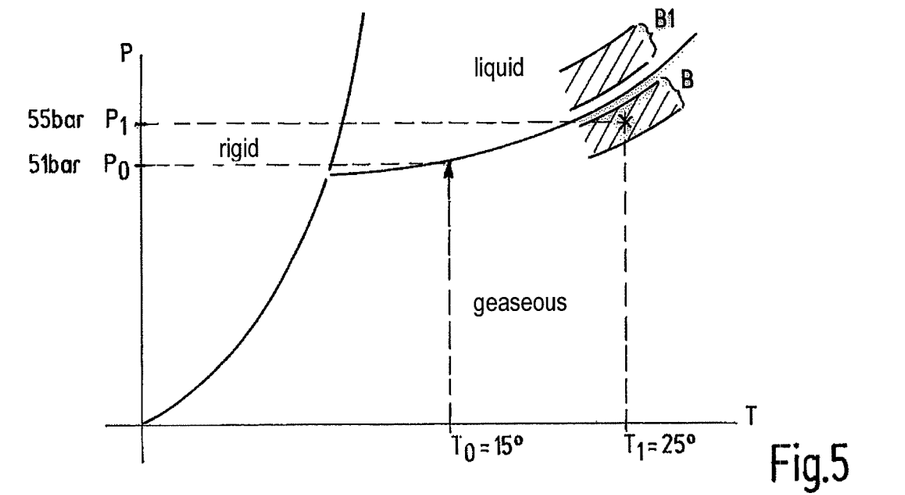
FIG. 5 shows a schematic phase diagram for a coolant.

During operation the coolant K coming from the storage container 15 is compressed by the pump 17, such that it enters the buffer container 19 under a pressure of more than 55 bar. For this FIG. 5 illustrates the phase diagram of $CO_2$. In the storage container 15 the coolant K is present in liquid as well as gaseous (vapor) phase. Its condition is thus located on the phase boundary between liquid and gaseous phase at $T_0$ and $P_0$. Thus, it is provided as saturated vapor.

The compression of the coolant in the pump 17 leads to a temperature increase first, such that the pressure increase does not necessarily result in liquefaction. However, a subsequent cooling of the coolant to room temperature may potentially result in that it crosses the phase boundary and forms droplets. Due to tempering of the buffer container 19 by heating thereof, its temperature is however increased to the temperature $T_1$, e.g. 25° C., that it is located in a region B of the area for the gaseous state of aggregation, as apparent from FIG. 5, wherein the region B is located with safety distance to the phase boundary. In the buffer container 19 the coolant K is preferably exclusively present in gaseous phase. However, on the bottom of the buffer container 19 also a part of the coolant K can at least temporarily deposit also in liquid phase.

The control device 28 can be configured to regulate the temperature and as appropriate also the pressure in the buffer container 19 such that the region B (see FIG. 5) is not left and the coolant K does not form condensate on its path up into the expansion chamber 14. Thereby the intensity of the cold production of the instrument 11 can be regulated by the flow controller (mass flow controller) 24 by means of which the coolant flow is controlled. Thereby the flow controller 24 can be controlled by the control device 28 that is in turn connected with an activation switch, for example, that has to be operated manually.

Numerous modifications can be made to the described device 10 and its mode of operation. For example, the apparatus 10 can be configured to take the coolant K in a gaseous or vapor state from the storage container 15, but to provide it at the supply connection 22 in liquid condition. For this the buffer container 19 can be configured as condensation container. The coolant K is collected in the buffer container at least partly in liquid phase. In this embodiment the tempering device 27 can be a heating as well or also a cooling device. A coolant can be supplied to the instrument 11 in liquid state in order to evaporate in the expansion chamber 14 thereby achieving a respective cooling effect. In this case the tempering of the buffer container 19—and if applicable additional elements, such as pipes 18, 20 and the pressure control valve 21—avoids a vapor bubble creation in the coolant K before it reaches the expansion chamber 14. The tempering device 27 ensures that the phase state of the coolant K is in the region B1 according to FIG. 5. The region B1 is arranged in the area for the liquid state of aggregation with safety distance to the phase boundary.

Figure 5A:
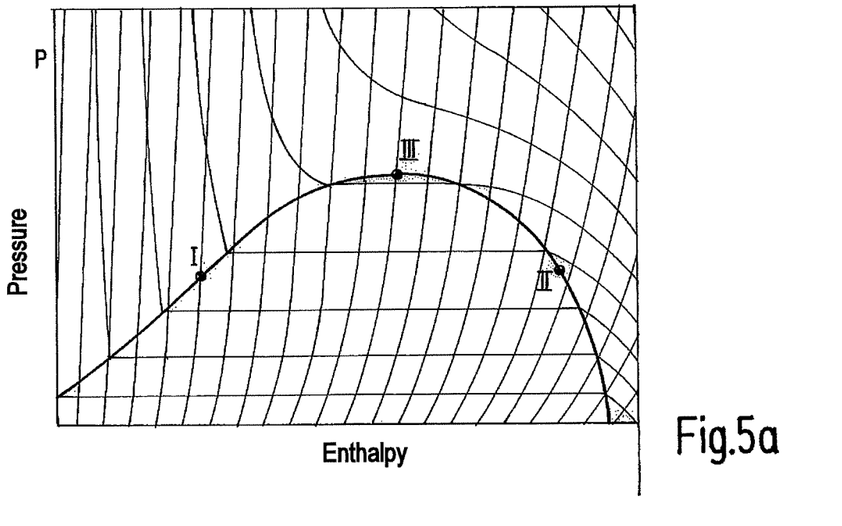
FIG. 5a shows an enthalpy-pressure-diagram for a coolant.

In FIG. 5A an enthalpy-pressure-diagram of a coolant, e.g. $CO_2$, is illustrated having a boiling curve I, a dew curve II and a critical point III. Between the boiling curve I and the dew curve II a region is located below the critical point III in which the coolant is provided in liquid as well as vapor phase. The vapor content of the mixture is characterized by isovapor curves that intersect the abscissa. The isothermal curves cross the wet vapor area. Therein the ratio of vapor to liquid (i.e. the vapor saturation) cannot be determined from the pressure and temperature. Therefore, in proximity of the boiling curve I and the dew curve II, as well as therebetween it cannot be determined whether the coolant is provided as gas, liquid or as two-phase-mixture by measurement of the pressure and temperature. The correct operation of the instrument, however, depends from the correct condition of the coolant. For this a vapor saturation sensor 29-$d$ can be provided in the pipe leading to the supply connection 22 or at another suitable location of the apparatus 10, as schematically illustrated in FIG. 1 and described in the following. The vapor saturation sensor 29-$d$ can be provided in addition or alternatively to the other sensors in the apparatus 10. The vapor saturation sensor 29-$d$ may be provided accordingly in all of the embodiments of the inventive apparatus 10.

Figure 2:
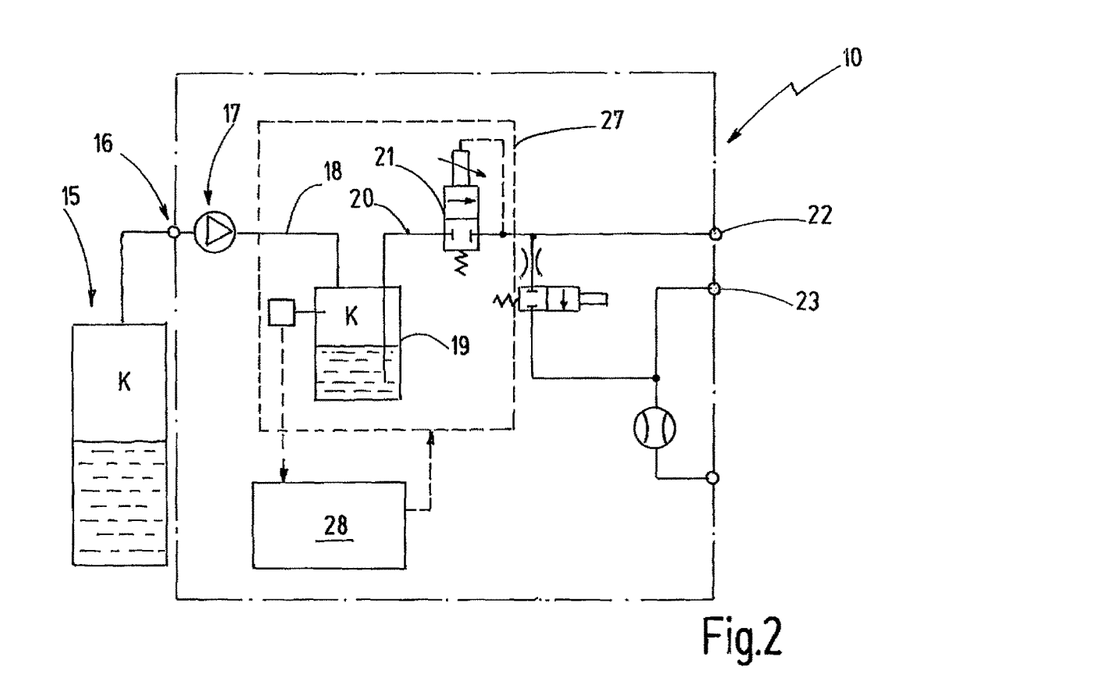
FIGS. 2-4 show additional embodiments of an apparatus for supply of a medical instrument in a schematic simplified illustration in each case.

In the embodiment of the apparatus 10 according to FIG. 2, the coolant K does not necessarily have be taken in gaseous condition from the storage container 15. It is also possible to provide the coolant K in liquid condition to the pump 17 and the buffer container 19, e.g. in that the storage container 15 is provided with a respective standpipe or is arranged upside down.

Figure 3:
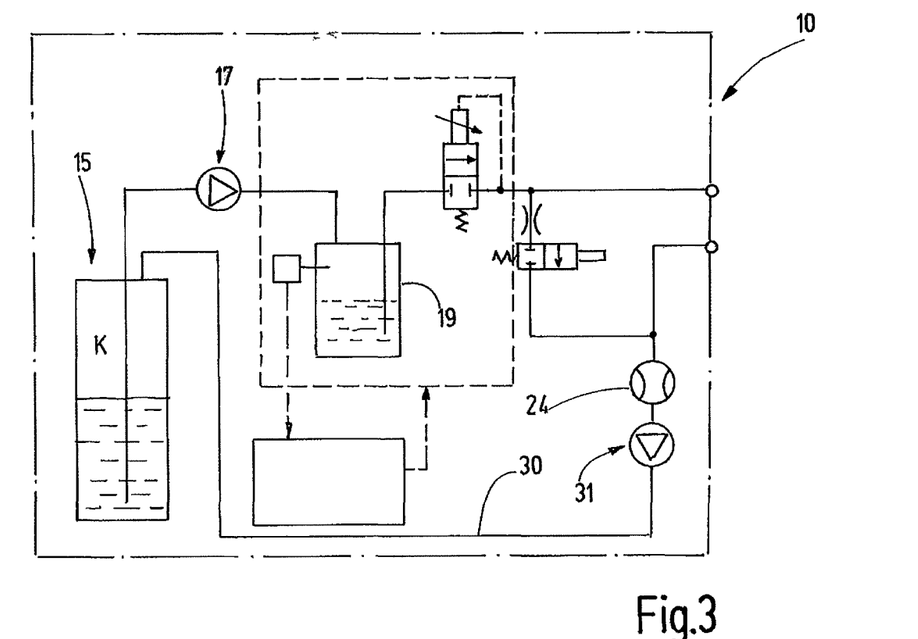

In all of the described embodiments the storage container 15 can be a separate container, e.g. a gas bottle, and can be connected to the connection 16 or as an alternative can be configured as storage container being part of the apparatus 10. The latter is illustrated in FIG. 3, wherein no outlet is provided there in order to release used coolant into the environment. Rather the flow controller/sensor 24 is connected to a return pipe 30 in which a pump 31 is arranged. The return pipe 30 leads to the storage container 15 that can be configured as condensation container, for example, in order to provide coolant K at least partly in liquid phase. Apart therefrom the apparatus 10 can be configured and can operate as described above, e.g. in connection with FIG. 2.

It is also possible to only provide a buffer container 19 instead of the storage container 15 and the buffer container 19, as well as the pump 17 arranged therebetween and to connect the return pipe 30 directly to the buffer container 19. In this case the storage container 15 and the pump 17 are omitted, wherein the pump 31 creates a pressure sufficient for supply of the buffer container 19.

Figure 4:
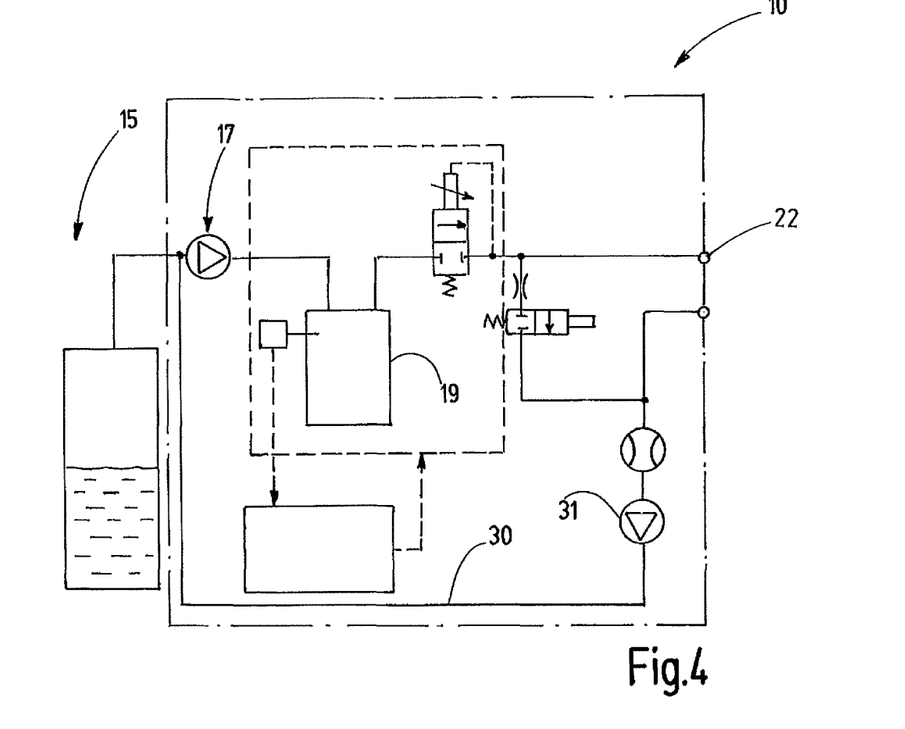

FIG. 4 illustrates an embodiment of the apparatus 10 similar to FIG. 3, however, with external storage container 15 that does not form part of the apparatus, e.g. again in the form of a gas bottle. The return pipe 30 is connected with the suction connection of the pump 17. Alternatively, it can also be connected with the buffer container 19, if the pump 31 allows a respective pressure creation. The apparatus 10 can be configured for supply of gaseous coolant K to the instrument, as illustrated in FIG. 4 or also for supply of liquid coolant K according to FIG. 3. The tempering device 27 is controlled by the control device 28 in each case such that the coolant is located in the phase diagram according to FIG. 5, either in the desired safe region B or in the desired safe liquid region B1.

In addition the apparatus 10 can comprise an instrument recognition device 32 in all of the embodiments (FIG. 1). The instrument recognition device 32 can be particularly configured to detect the necessary pressure for the operation of the instrument or to distinguish whether the instrument 11 has to be supplied with liquid or gaseous coolant. Accordingly, the tempering device 27 can be configured as heating or cooling device in order to transfer the coolant K as required in the region B or B1 of the phase diagram according to FIG. 5.

Figures 7, 8:
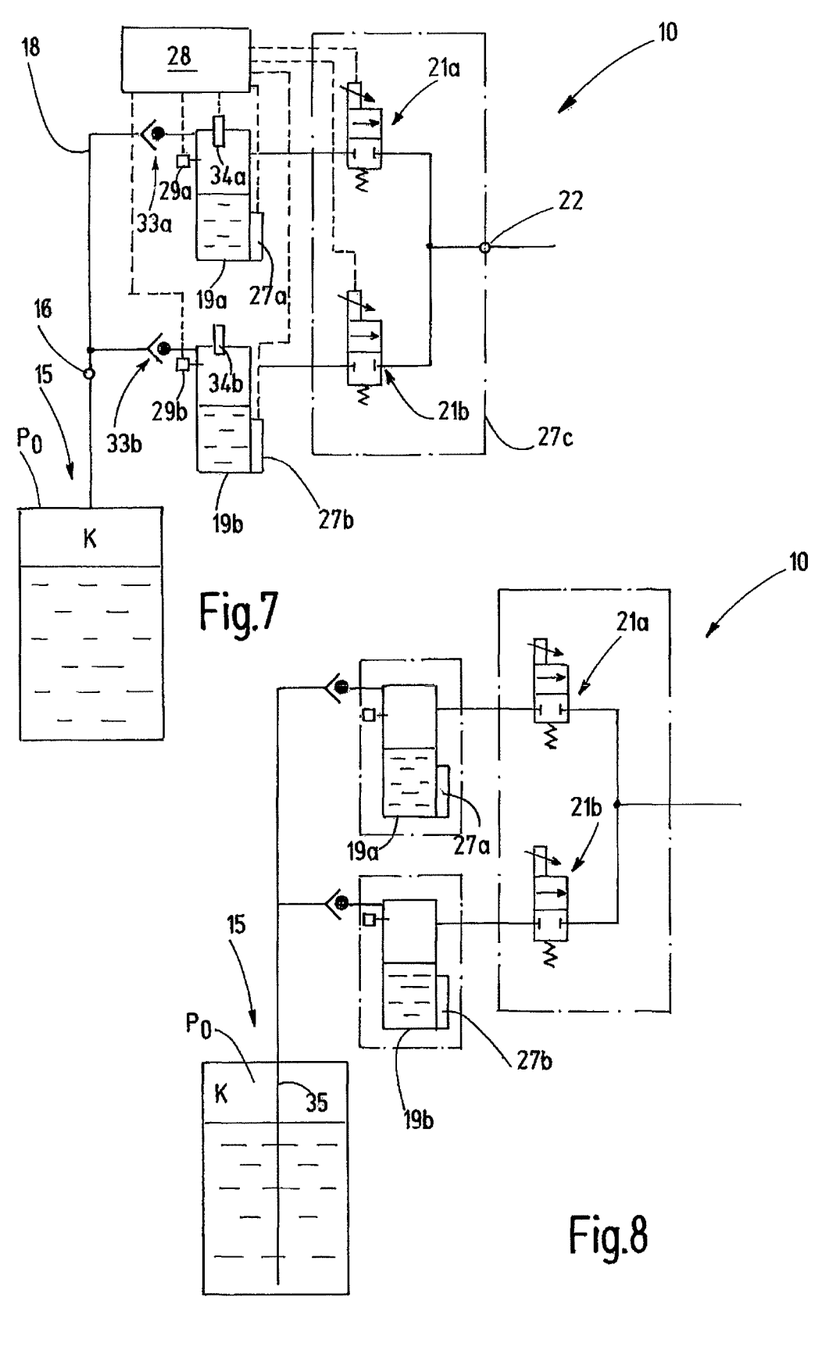
FIG. 7 shows an embodiment of an inventive apparatus with thermal compression of the coolant.
FIG. 8 shows a modified embodiment of an inventive apparatus with thermal compression of the coolant.

The apparatus 10 described so far operate with mechanical compression. However apparatus 10 are illustrated in FIGS. 7 and 8 that operate with thermal compression of the coolant K. For this the apparatus 10, according to FIG. 7, comprises a first buffer container 19$a$, as well as a second buffer container 19b that are both connected with the storage container 15 by means of a check valve 33a or 33b respectively. A mechanical pump is not provided in the respective pipe 18. If necessary, however, such a pump can be provided. The check valves 33a, 33b are configured to allow a flow from the storage container 15 in the respective buffer container 19a, 19b, but to block a respective return flow.

The two buffer containers 19a, 19b are respectively connected with a tempering device 27a, 27b that are preferably configured as Peltier-elements. The tempering devices 27a, 27b assigned to the respective buffer containers 19a, 19b are connected with the control device 28 in order to operate, for example, alternatingly or timely offset with regard to one another in the cooling operation or in the heating operation. The tempering devices 27a, 27b configured as Peltier-elements are configured to increase or lower the temperature in the respective buffer container 19a, 19b relative to the room temperature.

The two buffer containers 19a, 19b are in each case connected with the supply connection 22 via pressure control valves 21a, 21b. The pressure control valves 21a, 21b can also be connected with a common or with separate tempering device(s) 27c that can be preferably configured as exclusive heating devices. The pressure control valves 21a, 21b can be exclusively configured in pressure controlled manner, as described with regard to the embodiments above. In addition or as an alternative, they can be controlled by the control device 28 in order to close, if the respective upstream buffer container 19a, 19b is not heated, but cooled. Apart therefrom, the above description applies for the apparatus 10 according to FIG. 7.

The apparatus 10 according to FIG. 7 operates as follows:

For the explanation of the operation it is first assumed that both buffer containers 19a, 19b are empty. First, coolant ($CO_2$) from the storage container 15 enters the buffer containers 19a, 19b via the pipe 18 and the two check valves 33a, 33b until a pressure compensation is achieved. At least one of the two buffer containers 19a, 19b, e.g. the buffer container 19a, is now cooled by means of the tempering device 27a. In doing so, the coolant can condensate, whereby due to the occurring pressure decrease, additional coolant flows in via check valve 33a. Condensate is formed in the buffer container 19a, the level of which increases until the level sensor 29a triggers and indicates the level to the control device 28. The control device 28 terminates the cooling phase and deactivates the cooling operation of the tempering device 27a. The apparatus 10 is now ready for operation in order to supply a connected instrument. For this the tempering device 27a is transferred into the heating operation in order to heat the buffer container 19a and to create the desired pressure. Instantly the tempering device 27b can effect condensation of coolant K flowing into the buffer container 19b in cooling operation and can thus effect the filling thereof with condensate until a non-illustrated level sensor triggers. With this the cooling phase of the buffer container 19b can be terminated.

The supply connection 22 can now be continued under continuous heating or tempering of the buffer container 19a until the condensate present in the buffer container 19a is consumed thus far that the pressure sensor 29 indicates a decreasing pressure. The control device 28 now transfers the tempering device 27b into heating operation in order to build up the necessary operating pressure in the buffer container 19b. In addition, it activates the tempering device 27a in cooling operation in order to refill the buffer container 19a again with coolant condensate.

The heating and cooling phases in the two buffer containers 19a, 19b can alternate such that the necessary input pressure is always provided at the two pressure control valves 21a, 21b. In addition, the pressure control valves 21a, 21b can be kept warm by means of the tempering device 27c in order to avoid condensation of the coolant in the pressure control valves 21a, 21b as well as in the supplying and returning pipes.

The apparatus 10 according to FIG. 8 is basically similarly configured. However, the storage container 15 comprises a stand pipe 35 different to the apparatus 10 according to FIG. 7 such that liquid coolant is supplied to the buffer container 19a, 19b that is cooled respectively. This shortens the filling phases for the buffer containers 19a, 19b as well as reduces the cooling power required for the filling of the respective buffer container 19a, 19b. Apart therefrom, the description of device 10 according to FIG. 7 applies accordingly for the apparatus 10 according to FIG. 8.

Figures 9, 10:
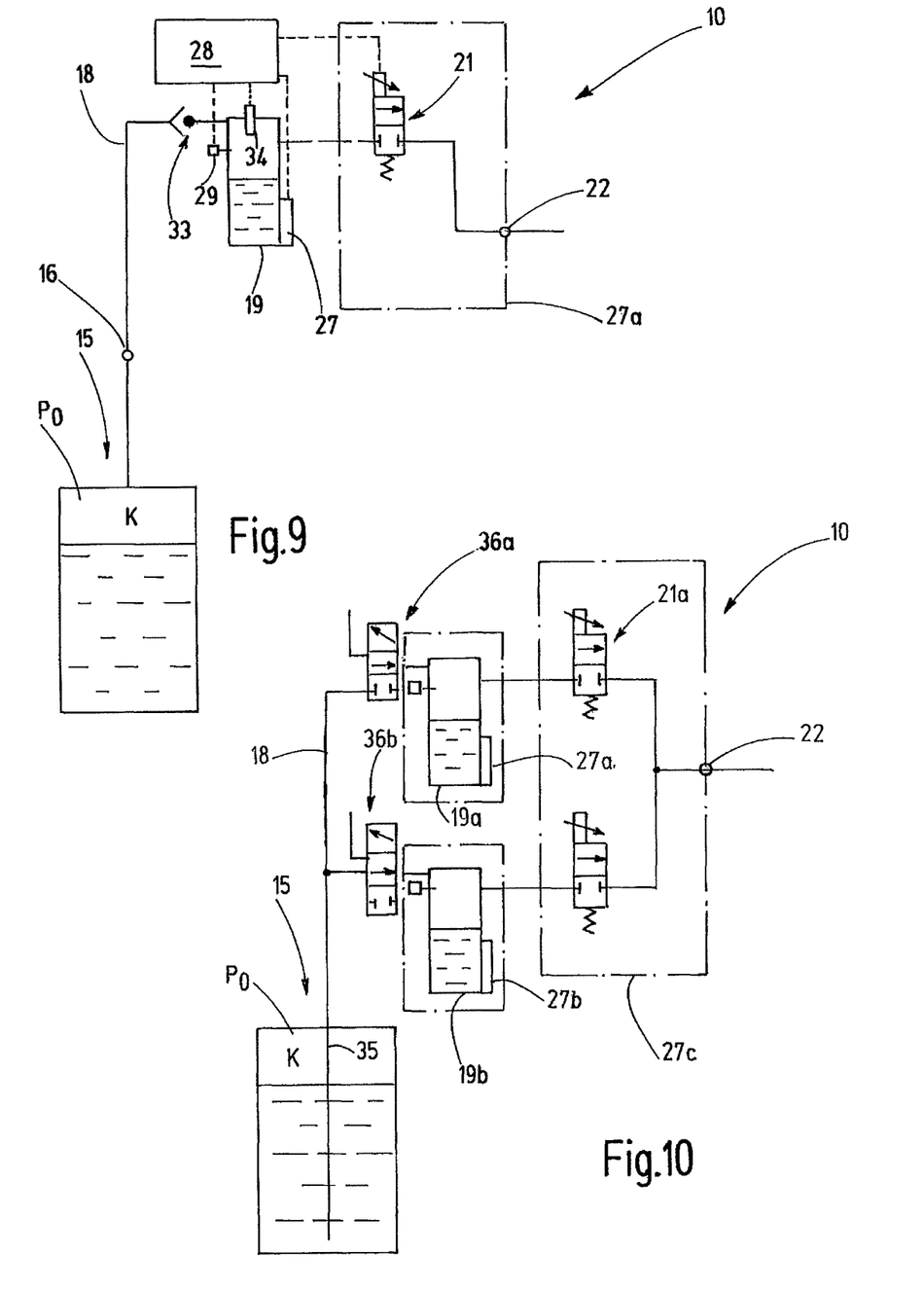
FIG. 9 shows an embodiment of an inventive apparatus with thermal compression of the coolant in a simplified embodiment.
FIG. 10 shows another modified embodiment of an inventive apparatus with thermal compression of the coolant.

The apparatus 10 according to FIG. 7 is configured to continuously supply gas at the supply connection 22 in that the two buffer containers 19a, 19b are alternately heated and cooled. In addition, FIG. 9 illustrates a simplified version of the apparatus that is configured to supply coolant with the desired pressure and temperature at the supply connection 22 at least for a certain time. For tempering the coolant, only one single buffer container 19 is provided in which a low pressure can be created by cooling by means of the tempering device 27 that allows coolant to flow in the buffer container 19 and to condensate. Alternatively, the storage container 15 can be provided with a stand pipe 35 different to the illustration in FIG. 9 or can be arranged upside down such that during cooling of the buffer container 19 liquid coolant flows therein.

After this filling phase the buffer container 19 can be heated by means of the tempering device 27 such that the desired higher pressure is achieved in the buffer container 19. Now it is possible to provide coolant with the desired pressure and the desired temperature at the supply connection 22 until the supply in the buffer container 19 is depleted. The size of the buffer container can be dimensioned so large, such that the provided supply is sufficient for carrying out one or more surgeries.

Another modified device 10 is illustrated in FIG. 10. The particularity of this device is that the buffer containers 19a, 19b are connected with tempering devices 27a, 27b that only provide a heating function, but no cooling function, such as for example electrical heating resistors. Instead of check valves 33a, 33b, however, way valves 36a, 36b are provided in the apparatus 10 according to FIG. 10 that either connect the buffer container 19a, 19b with the storage container 15 or vent it toward the environment. Instead of the way valves 36a, 36b, also other controlled valves can be provided, e.g. one on/off-valve in the pipe 18 and another controlled on/off-valve for venting of the respective buffer container. The way valves 36a, 36b or the other valves are controlled by the control device 28 that is not illustrated in FIG. 10. For explanation of the function it is first assumed that both buffer containers 19a, 19b are filled with coolant. If now, for example, the buffer container 19a is heated by means of the tempering device 27a and if the way valve 36a is closed, the pressure in the buffer container 19a increases up to the desired value. By means of the pressure control valve 21a coolant can now be supplied with the desired pressure at the supply connection 22.

Concurrently, the buffer container 19b can be filled with coolant. For this it is first vented by means of the way valve 36b and thus made pressureless. Subsequently, the buffer container 19*b* is connected with the pipe 18 via the way valve 36*b* such that coolant can flow into the buffer container 19*b* via the stand pipe 35 and the way valve 36*b* until a pressure compensation has been achieved. The way valve 36*b* can now close such that the buffer container 19*b* is ready for supply of coolant. Before such supply is desired, the control device 28 switches the heating device 27*b* on in order to temper the buffer container 19*b* and thus to bring it to the desired temperature and the desired pressure, whereby the buffer container 19*b* is ready for supply. Now at least for a short term, both buffer containers 19*a*, 19*b* can supply coolant, whereby it is assumed that the coolant supply in the buffer container 19*a* depletes or is completely depleted. As soon as this is the case, the tempering device 27*a* is deactivated such that the buffer container 19*a* can cool down again. In addition, the way valve 36*a* can now be used in order to deplete the remaining pressure from the buffer container 19*a* and thus to make the buffer container 19*a* pressureless. If this has been accomplished, the buffer container 19*a* can be connected to the storage container 15 by means of the way valve 36*a* such that coolant flows in the buffer container 19*a* and fills it until pressure compensation has been achieved. At this point of time, the way valve 36*a* can close again and can thus be transferred in the position illustrated in FIG. 10. After the activation of the tempering device 27*a* and sufficient heating of the buffer container 19*a* by means thereof, the buffer container 19*a* is ready for supply. Thus, both buffer containers 19*a*, 19*b* can be alternatingly filled and tempered in order to supply coolant with the desired pressure and desired temperature at the supply connection 22 in a timely alternating manner or also with a timely overlap. In a simplified version of the apparatus 10 according to FIG. 10 only one single buffer container 19 is present that is alternatingly made pressureless by means of the way valve 36*a* and is then filled and subsequently separated from the storage container and heated in order to provide the received coolant supply with the desired pressure and the desired temperature. The operation is then similar to the apparatus 10 according to FIG. 9 with the difference that the pressure reduction necessary for the filling of the buffer container 19*a* is not achieved by cooling of the buffer container 19*a*, but by venting to the atmosphere.

Also in the apparatus 10, according to FIG. 9 or 10 and in the modified embodiments derived therefrom, a pump may be arranged in the pipe 18 for support of the filling of the respective buffer container 19, 19*a*, 19*b*.

Figure 11:
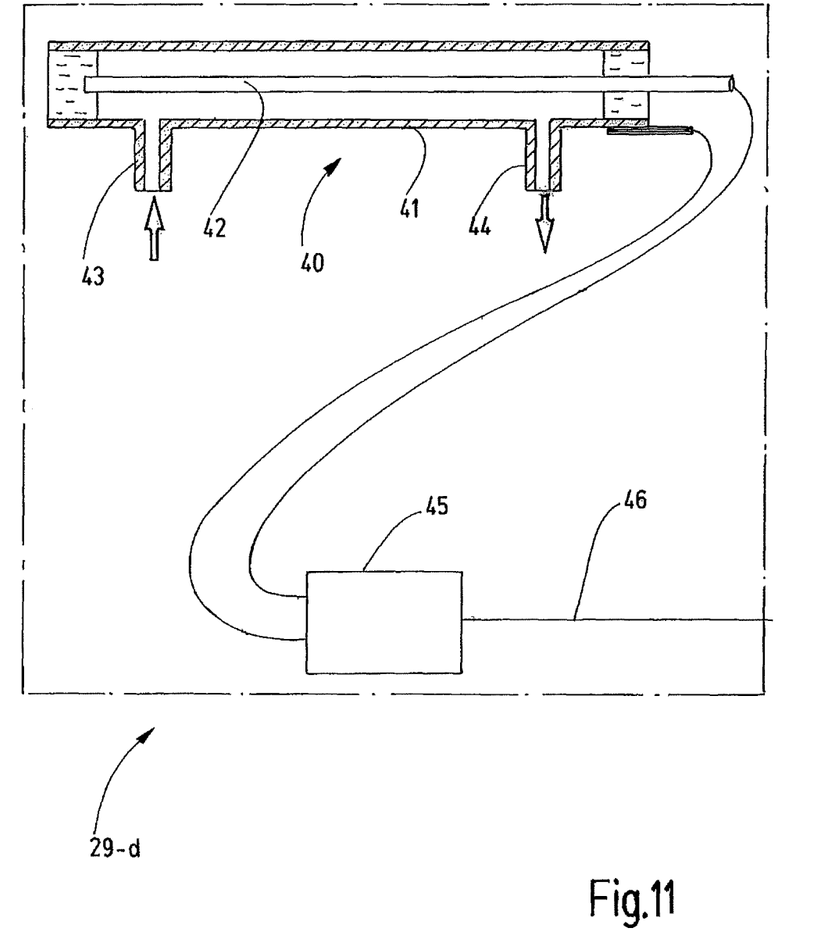
FIG. 11 shows a vapor saturation sensor in a schematic illustration.

FIG. 11 schematically illustrates the vapor saturation sensor 29-*d*. The vapor saturation sensor 29-*d* is configured as capacitive sensor. For this it comprises a capacitor 40 through which the fluid, the condition of which has to be determined, is channeled as dielectric. The capacitor 40 comprises a tube-shaped housing 41 that is used as outer electrode and in the inner space of which a second, e.g. rod-shaped electrode 42 is arranged. The housing 41 is sealingly closed at both ends, wherein the electrode 42 extends out of the housing 41. In addition, two connections 43, 44 are provided on the housing 41 for supply and return of the fluid, the condition of which has to be determined.

The two electrodes, i.e. the housing 41 and the electrode 42, are connected with an electrical circuit 45 via suitable electrical connections, wherein the circuit 45 serves for determination of the capacity between the electrode 42 and the housing 41. The circuit can use any suitable capacity measuring method. Dependent on the determined capacity, it creates a signal at its output 46 characterizing the measured capacity and thus the vapor saturation of the fluid channel through the capacitor 40, wherein the signal is supplied to the control device 28.

It is further possible to provide a temperature sensor that detects the temperature of the coolant flowing through the capacitor in direct proximity to the vapor saturation sensor 29-*d*. It can be provided to determine the pressure of the coolant from the measured vapor saturation and the measured temperature, at least if the condition of the coolant is located between the boiling curve I and the dew curve II (FIG. 5*a*).

The apparatus 10 for supply of coolant, particularly $CO_2$ that is preferably provided in bottles, to cryosurgical instruments can comprise a mechanical or thermal compression device. For this a pump 17 can be provided in order to supply the $CO_2$ taken from the bottle in a buffer container 19 with a desired operation pressure, wherein the pressure in the gas bottle can be less than the desired operation pressure. The apparatus 10 comprises a tempering device 27 that is configured to bring the coolant to a desired temperature, particularly a temperature that is higher than the temperature in the gas bottle or in another storage container 15. In so doing, a safe supply of a cryosurgical instrument with coolant having the desired pressure and sufficient temperature is ensured. Particularly, undesired droplet creation in the instrument or supplying pipes is avoided.

The invention claimed is:

1. A device for supply of $CO_2$ coolant to a medical instrument, the device comprising:
    a storage container configured for storage of a first supply of $CO_2$ coolant in compressed condition with a first pressure $P_0$ sufficiently low to maintain coolant in a gaseous phase at temperatures between about 15° C. and 25° C.;
    a control device containing:
        a buffer container configured for storage of a second supply of $CO_2$ coolant in compressed condition with a second pressure $P_1$, higher than the first pressure $P_0$, sufficiently low to maintain the coolant in a gaseous phase having no droplets at temperatures between about 15° C. and 25° C.; and
        a tempering device configured to actively heat the buffer container and $CO_2$ coolant; and
    an instrument configured to receive the coolant as a gas.

2. The device according to claim 1, wherein a pump is provided that is connected with the storage container on a suction side and with the buffer container on a pressure side.

3. The device according to claim 1, further comprising a vapor saturation sensor.

4. The device according to claim 2, characterized in that the pump is a displacement pump.

5. The device according to claim 1, wherein a pressure control valve is arranged between the buffer container and a supply connection for supply of coolant to a cryosurgical instrument.

6. The device according to claim 2, further comprising:
    an instrument recognition device connected with the pump and/or the tempering device in order to provide the coolant in a condition predefined for the instrument.

7. The device according to claim 5, wherein the tempering device is connected with the pressure control valve.

8. The device according to claim 6, wherein the tempering device is connected with pipes that connect the buffer container with the pump and/or the buffer container with a pressure control valve.

9. The device according to claim 1, further comprising a return connection.

10. The device according to claim 9, characterized in that the return connection is connected with a mass flow sensor.

11. The device according to claim 9, wherein a return flow pump is arranged between the return connection and the storage container.

12. A method for providing a coolant for a medical instrument, the method comprising:
taking coolant from a storage container at a first pressure $P_0$; sufficiently low to maintain coolant in a gaseous phase at temperatures between about 15° C. and 25° C.
conveying coolant in a buffer container;
increasing the pressure of the coolant during the conveyance in the buffer container or after the conveyance while maintaining the coolant in a gaseous phase at temperatures between about 15° C. and 25° C.; and
actively heating the coolant in the buffer container during and/or after its compression sufficient to supply the coolant to a supply connection in the gaseous phase.

13. The method according to claim 12, wherein the coolant is taken from the storage container as saturated vapor and is compressed by a pump in order to increase its pressure.

14. The method according to claim 12, wherein the pressure and the temperature in the buffer container is adjusted such that the coolant in the buffer container is provided in gaseous phase exclusively or that the pressure and the temperature in the buffer container is adjusted such that the coolant in the buffer container is provided at least in part in liquid phase and in another part in gaseous phase or that the pressure and the temperature in the buffer container is adjusted such that the coolant in the buffer container is provided in the liquid phase exclusively.

\* \* \* \* \*